(12) United States Patent
Chelak (10) Patent No.: US 8,506,538 B2
(45) Date of Patent: Aug. 13, 2013

(54) DEVICE FOR REDUCING MICROBIAL CONTAMINATION

(75) Inventor: Todd M. Chelak, Westborough, MA (US)

(73) Assignee: Covidien LP, Mansfield, MA (US)

( * ) Notice: Subject to any disclaimer, the term of this patent is extended or adjusted under 35 U.S.C. 154(b) by 324 days.

(21) Appl. No.: 12/328,809

(22) Filed: Dec. 5, 2008

(65) Prior Publication Data

US 2009/0149819 A1   Jun. 11, 2009

Related U.S. Application Data

(60) Provisional application No. 60/992,539, filed on Dec. 5, 2007.

(51) Int. Cl.
*A61M 5/32* (2006.01)

(52) U.S. Cl.
USPC ............................................ 604/265; 604/533

(58) Field of Classification Search
USPC ......... 604/265–267, 256, 905, 289; 220/380; 422/292
See application file for complete search history.

(56) References Cited

U.S. PATENT DOCUMENTS

| | | | |
|---|---|---|---|
| 4,232,677 A * | 11/1980 | Leibinsohn | 604/247 |
| 4,662,878 A | 5/1987 | Lindmayer | |
| 4,778,447 A | 10/1988 | Velde et al. | |
| 4,883,483 A | 11/1989 | Lindmayer | |
| 5,298,024 A | 3/1994 | Richmond | |
| 5,360,413 A | 11/1994 | Leason et al. | |
| 5,395,348 A | 3/1995 | Ryan | |
| 5,401,245 A | 3/1995 | Haining | |
| 5,405,333 A | 4/1995 | Richmond | |
| 5,470,319 A | 11/1995 | Mayer | |
| 5,476,449 A | 12/1995 | Richmond | |
| 5,533,983 A | 7/1996 | Haining | |

(Continued)

FOREIGN PATENT DOCUMENTS

| | | |
|---|---|---|
| EP | 0 227 219 | 7/1987 |
| EP | 2 067 500 | 6/2009 |
| WO | WO 2006/019782 A2 | 2/2006 |
| WO | WO 2008/089196 A2 | 7/2008 |

OTHER PUBLICATIONS

Japanese Office Action from Japanese Appln. No. 2008-309689 mailed Feb. 27, 2013.

(Continued)

*Primary Examiner* — Kevin C Sirmons
*Assistant Examiner* — Brandy S Lee
(74) *Attorney, Agent, or Firm* — Lisa E. Winsor, Esq.

(57) ABSTRACT

A medical device for use in connection with a connector of an indwelling line for cleansing a surface of a septum of the connector is provided. The medical device includes a housing including a proximal portion defining a cavity containing a quantity of microbial reducing agent, a distal portion defining a cavity for selective coupling with the connector of the indwelling line, and a partition separating the proximal and distal cavities, wherein the proximal and distal cavities are in fluid communication with one another; and a deformable member overlying an end of the proximal portion for maintaining the microbial reducing agent within the proximal cavity thereof. The microbial reducing agent being dispensable into the distal cavity, at least when the medical device is connected to the connector of the indwelling line, to awash a surface of the connector of the indwelling line and reduce microbes present thereon.

17 Claims, 5 Drawing Sheets

(56) References Cited

U.S. PATENT DOCUMENTS

| | | | |
|---|---|---|---|
| 5,549,577 A | 8/1996 | Siegel et al. | |
| 5,552,118 A | 9/1996 | Mayer | |
| 5,573,516 A | 11/1996 | Tyner | |
| 5,597,536 A | 1/1997 | Mayer | |
| 5,616,130 A | 4/1997 | Mayer | |
| 5,676,346 A | 10/1997 | Leinsing | |
| 5,743,894 A | 4/1998 | Swisher | |
| 5,785,693 A | 7/1998 | Haining | |
| 5,820,601 A | 10/1998 | Mayer | |
| 5,833,674 A | 11/1998 | Turnbull et al. | |
| 5,836,923 A | 11/1998 | Mayer | |
| 5,848,994 A | 12/1998 | Richmond | |
| 5,957,898 A | 9/1999 | Jepson et al. | |
| 5,971,965 A | 10/1999 | Mayer | |
| 6,029,946 A | 2/2000 | Doyle | |
| 6,036,171 A | 3/2000 | Weinheimer et al. | |
| 6,045,539 A * | 4/2000 | Menyhay | 604/256 |
| 6,048,335 A | 4/2000 | Mayer | |
| 6,089,541 A * | 7/2000 | Weinheimer et al. | 251/149.6 |
| 6,146,362 A | 11/2000 | Turnbull et al. | |
| 6,183,448 B1 | 2/2001 | Mayer | |
| 6,206,860 B1 | 3/2001 | Richmond | |
| 6,210,624 B1 | 4/2001 | Mayer | |
| 6,290,206 B1 | 9/2001 | Doyle | |
| 6,485,472 B1 | 11/2002 | Richmond | |
| 6,541,802 B2 | 4/2003 | Doyle | |
| 6,572,591 B2 | 6/2003 | Mayer | |
| 6,651,956 B2 | 11/2003 | Miller | |
| 6,666,852 B2 | 12/2003 | Niedospial, Jr. | |
| 6,706,022 B1 | 3/2004 | Leinsing et al. | |
| 6,840,501 B2 | 1/2005 | Doyle | |
| 7,081,109 B2 | 7/2006 | Tighe et al. | |
| 7,118,560 B2 | 10/2006 | Bonaldo | |
| 7,184,825 B2 | 2/2007 | Leinsing et al. | |
| 7,291,134 B2 | 11/2007 | Fitzgerald | |
| 2001/0045539 A1 | 11/2001 | Doyle | |
| 2002/0066715 A1 | 6/2002 | Niedospial, Jr. | |
| 2002/0133124 A1 | 9/2002 | Leinsing et al. | |
| 2003/0183795 A1 | 10/2003 | Doyle | |
| 2003/0199835 A1 | 10/2003 | Leinsing et al. | |
| 2003/0233074 A1 | 12/2003 | Shields | |
| 2004/0171993 A1 | 9/2004 | Bonaldo | |
| 2004/0172006 A1 | 9/2004 | Bonaldo | |
| 2005/0147525 A1 | 7/2005 | Bousquet | |
| 2005/0222542 A1 * | 10/2005 | Burkholz et al. | 604/289 |
| 2005/0241668 A1 | 11/2005 | Trampuz et al. | |
| 2006/0025724 A1 | 2/2006 | Chen | |
| 2006/0089605 A1 | 4/2006 | Fitzgerald | |
| 2006/0217671 A1 | 9/2006 | Peppel | |
| 2006/0286155 A1 * | 12/2006 | Trotter et al. | 424/445 |
| 2007/0112333 A1 * | 5/2007 | Hoang et al. | 604/533 |
| 2007/0218757 A1 | 9/2007 | Guala | |
| 2007/0260195 A1 | 11/2007 | Bartholomew et al. | |

OTHER PUBLICATIONS

Mexican Office Action from Mexican Appln. No. MX/a/2008/015262 dated Mar. 8, 2013.

* cited by examiner

DEVICE FOR REDUCING MICROBIAL CONTAMINATION

CROSS-REFERENCE TO RELATED APPLICATION

The present application claims the benefit of U.S. Provisional Application No. 60/992,539, filed on Dec. 5, 2007, the entire content of which is incorporated herein by reference.

BACKGROUND

1. Technical Field

The present application relates to medical devices and, more particularly, to medical devices for use in connection with needleless connectors and the like for reducing the incidents of microbial contaminations on an external surface thereof.

2. Background of Related Art

Needleless connectors, commonly used with indwelling catheters, are typically accessed repeatedly by medical devices, such as, syringes, for the withdrawal of blood from a patient and/or the delivery/administration of medicaments to a patient. During entry of a syringe into a needleless connector, any microbes located on an external surface of the needleless connector, in particular on the access surface, may gain entry into the fluid path and then be introduced into the indwelling catheter, potentially resulting in bloodstream infections. Since conventional needleless connectors contain valve mechanisms that open a flow path upon connection of the syringe and close the flow path upon disconnection of the syringe, capping of needleless connectors between medical interventions is not commonplace.

As a result of these practices and in view of the concern for bloodstream infections, cleansing of the needleless connector prior to a medical intervention is recommended. The traditional cleansing method makes use of an alcohol swab which is wiped over the external access surface of the needleless connector. However, several factors, including a lack of convenience, lead to gaps in the usage of alcohol swabs and an increase in the potential for bloodstream infections.

Accordingly, a need exists for a more efficient system for reducing the potential of microbial contamination associated with needleless connectors.

SUMMARY

The present application relates to medical devices for use in connection with needleless connectors and the like for reducing the incidents of microbial contaminations on an external surface thereof.

According to an aspect of the present disclosure, a medical device for use in connection with a connector of an indwelling line is provided and includes a housing having a proximal portion and a distal portion separated from one another by a partition, wherein each of the proximal portion and the distal portion defines a respective proximal cavity and a distal cavity, wherein the proximal and distal cavities are in fluid communication with one another, and wherein the distal portion includes structure for selectively coupling with the connector of the indwelling line. The medical device further includes a microbial reducing agent disposed within the proximal cavity of the proximal portion; and a deformable member overlying an end of the proximal portion for maintaining the microbial reducing agent within the proximal cavity of the proximal portion.

The medical device may further include a valve member supported by the partition for enabling selective fluid communication between the proximal cavity and the distal cavity. The medical device may still further include an absorbent member disposed within the distal cavity.

The absorbent member may be dimensioned to contact the connector of the indwelling line when the medical device is connected thereto. The absorbent member may be in contact with the partition. The absorbent member may be axially slidably disposed within the distal cavity.

The medical device may further include a biasing member interposed between the partition and the absorbent member. The biasing member may maintain the absorbent member at a distal-most location.

The medical device may further include a backing member supporting the absorbent member. The backing member may be at least one of porous and permeable.

The absorbent member may be resilient. The absorbent member may contact an outer surface of the connector of the indwelling line when the medical device is connected to the connector of the indwelling line. The absorbent member may exert a mechanical cleansing action on at least a portion of the outer surface of the connector of the indwelling line upon a disconnection of the medical device from the connector of the indwelling line.

The microbial reducing agent may be transferable from the proximal cavity to the distal cavity upon exertion of a sufficient force on the deformable member. The microbial reducing agent may be transferred through the partition. The microbial reducing agent may be transferred through the valve member. The valve member may be a duck-bill valve.

The microbial reducing agent may be transferable to the absorbent member at least prior to an attachment of the medical device to the connector of the indwelling line and/or after an attachment of the medical device to the connector of the indwelling line. As such, the absorbent member may exert a chemical/biological and a mechanical cleansing action on an outer surface of the connector of the indwelling line upon at least connection and/or disconnection of the medical device to and/or from the connector of the indwelling line.

According to a further aspect of the present disclosure, a medical device for use in connection with a connector of an indwelling line for cleansing a surface of a septum of the connector is provided. The medical device includes a housing including a proximal portion defining a cavity containing a quantity of microbial reducing agent, a distal portion defining a cavity configured and dimensioned for selective coupling with the connector of the indwelling line, and a partition separating the proximal cavity and the distal cavity, wherein the proximal and distal cavities are in fluid communication with one another. The medical device further includes a deformable member overlying an end of the proximal portion for maintaining the microbial reducing agent within the proximal cavity of the proximal portion. In use, the microbial reducing agent is dispensable into the distal cavity, at least when the medical device is connected to the connector of the indwelling line, to awash a surface of the connector of the indwelling line and reduce microbes present thereon.

The medical device may further include an absorbent member disposed within the distal cavity. The absorbent member may be configured and dimensioned to contact the surface of the connector of the indwelling line when the medical device is connected thereto and to exert a mechanical cleansing action of the outer surface of the connector of the indwelling line when the medical device is at least connected to the connector of the indwelling line and/or disconnected from the connector of the indwelling line.

DETAILED DESCRIPTION OF THE DRAWINGS

DETAILED DESCRIPTION OF EMBODIMENTS

The following description is not intended to limit the claimed invention to the described embodiments and the disclosed combination of features in the various embodiments may not be absolutely necessary for the inventive solution.

Referring initially to FIGS. 1A-1D, a medical device, for reducing the incidents of microbial contaminations on an external surface of a needleless connector 10, is generally designated as 100. As used herein, and as is common in the art, the term "distal" will refer to those elements located further from a user and the term "proximal" will refer to those elements located closer to a user. Unless otherwise specified, each of the devices disclosed herein will have a generally circular transverse cross-sectional profile.

In general, a needleless connector, such as needleless connector 10, includes thickened septum 12 and a housing 14 to radially compress the septum 12 to thereby seal a slit 16 extending through the septum 12. Alternatively, needleless connectors with any type of septum configuration known in the art, such as a generally solid septum, may be used. Accordingly, in use, when a male luer tip of a syringe (not shown) is pressed against an outer surface 18 of the septum 12 to open the slit 16, an outer surface of the male luer tip disturbs the outer surface 18 of the septum 12, thereby potentially carrying with it any microbes present on the outer surface 18 of the septum 12 into the connector 10 (i.e., beyond the septum 12).

As seen in FIGS. 1A-1D, medical device 100 includes a housing 110 having a proximal end 112 and a distal end 114 separated from one another by a partition 116. Proximal end 112 defines a cavity or chamber 112a having an open proximal end 112b that is covered by a deformable member in the form of an impermeable membrane 118 or the like. It is contemplated that other configurations for proximal end 112 may be used, such as, for example, a closed configuration having at least one domed surface or deformable member located along the length of proximal end 112 and unitarily formed with housing 110. It is further contemplated that at least a portion of the wall thickness of the at least one domed surface or deformable member may be thinner than the adjacent structure of housing 110 which would facilitate the collapsing of the domed structure.

A microbial reducing agent "MRA" in liquid or gel form is retained within proximal cavity 112a. Suitable microbial reducing agents include and are not limited to alcohol, povidone iodine, ethylenediaminetetraacetic acid (EDTA), or any other agent or any combination of agents typically used for cleansing medical devices and/or inhibiting microbial contamination thereon. A sufficient quantity of microbial reducing agent "MRA" is retained within proximal cavity 112a such that membrane 118 projects from medical device 100 when medical device 100 is new and/or un-used.

Distal end 114 defines a cavity or chamber 114a having an open distal end 114b and being configured and dimensioned to selectively receive and engage needleless connector 100. Distal end 114 includes a coupling member 114c formed on or in an inner surface thereof for selectively engaging a complementary coupling member 14a provided on or in housing 14 of needleless connector 10. Coupling member 114c may include and is not limited to a helical thread, a bayonet-type connector, or any other suitable formation capable of establishing a mechanical connection between medical device 100 and housing 14 of needleless connector 10.

Partition 116 defines at least one opening 116a therein for fluidly interconnecting proximal cavity 112a and distal cavity 114a. Medical device 100 includes a valve member 120 disposed within each opening 116a. Valve member 120 may be a unidirectional valve, such as, for example, a duckbill valve, which allows for fluid flow in substantially a single direction from proximal cavity 112a to distal cavity 114a. It is contemplated that other types of valve members may be used, such as, for example, bi-direction valves which allow for fluid flow between proximal cavity 112a and distal cavity 114a. It is further contemplated that any element capable of maintaining the microbial reducing agent "MRA" within proximal cavity 112a and selectively releasing the microbial reducing agent "MRA" from within proximal cavity 112a may be used to occlude each opening 116a, such as, for example, a breakthrough seal or the like. When medical device 100 is new and/or un-used, valve member 120 maintains substantially all of the microbial reducing agent "MRA" within proximal cavity 112a.

Medical device 100 further includes an absorbent member 122, such as, for example, a sponge, a pad or the like disposed within distal cavity 114a of distal portion 114. Absorbent member 122 may be supported on a backing member 124 or the like. Backing member 124 may be porous, permeable or, alternatively, may include at least one aperture 124a formed therethrough. It is contemplated that apertures 124a may extend at least partially or completely through absorbent member 124 to more directly "wet out" the surface of septum 12.

A biasing member 126 may be interposed between partition 116 and absorbent member 122 for maintaining absorbent member 122 at a distal-most position within distal cavity 114a of distal end 114 when medical device 100 is not connected to needleless connector 10.

With continued reference to FIGS. 1A-1D, a method of using medical device 100 is provided below. In use, upon completion of a medical intervention, distal portion 114 of medical device 100 is connected to needleless connector 10. Medical device 100 remains connected to needleless connector 10 via the inter-engagement of respective coupling members 114c and 14a.

Figure 1A:
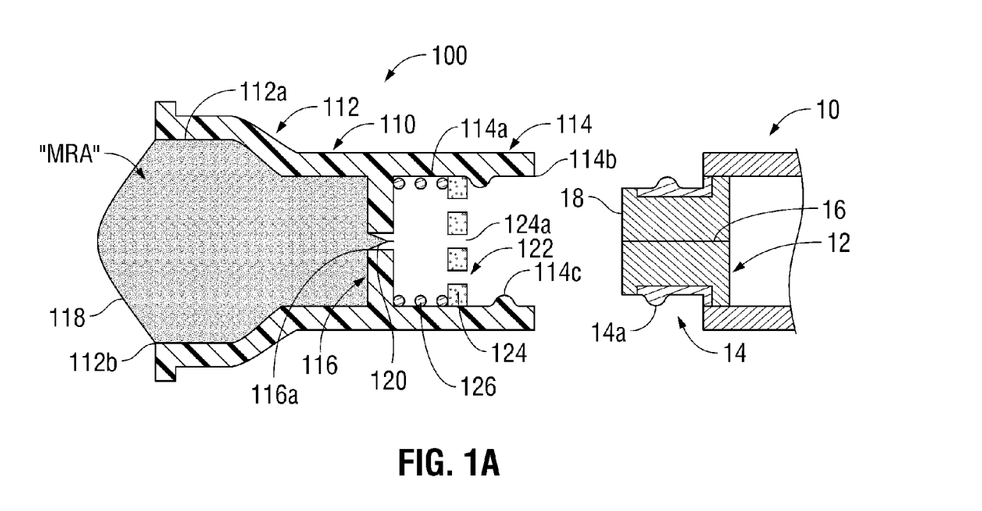
FIG. 1A is a schematic, longitudinal, cross-sectional view of a medical device, for use with a needleless connector, according to an embodiment of the present disclosure, shown in a first, un-used and pre-connected condition.
Figure 1B:
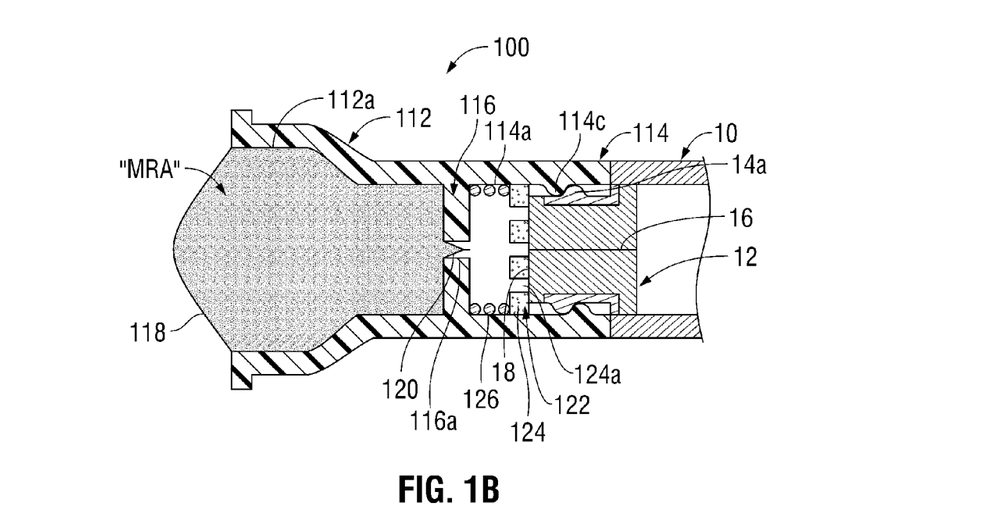
FIG. 1B is a schematic, longitudinal, cross-sectional view of the medical device of FIG. 1, shown connected to the needleless connector and in an un-used condition.

As seen in FIG. 1B, as medical device 100 is coupled to needleless connector 10, outer surface 18 of septum 12 thereof contacts and presses against absorbent member 122. Additionally, as medical device 100 is fully and/or completely coupled to needleless connector 10, biasing member 126 becomes compressed within distal cavity 114a and thus creates an increasing frictional force between absorbent member 122 and outer surface 18 of septum 12.

Figure 1C:
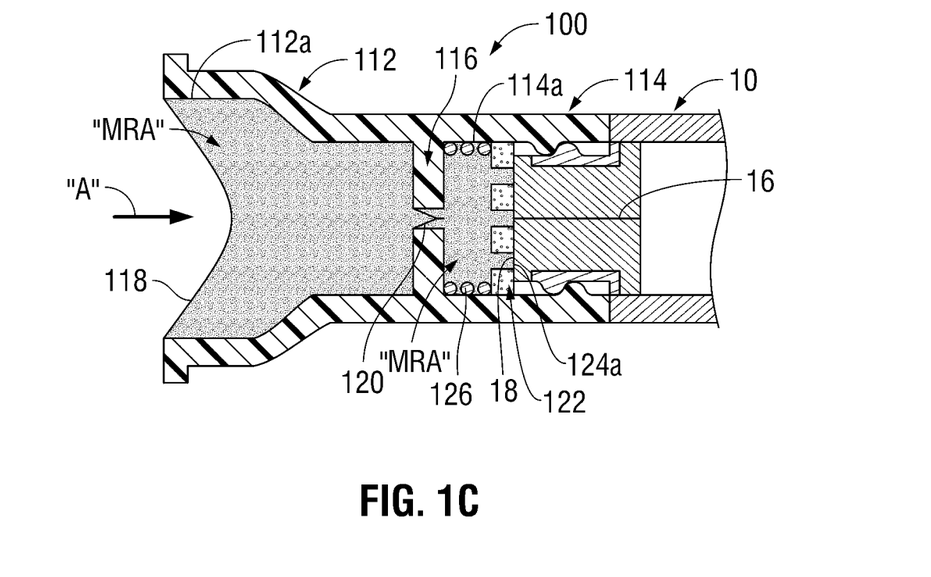
FIG. 1C is a schematic, longitudinal, cross-sectional view of the medical device of FIGS. 1A and 1B, shown in a primed condition.

In use, prior to a subsequent medical intervention, as seen in FIG. 1C, membrane 118 is pressed, in the direction of arrow "A", to create a fluid pressure within proximal cavity 112a of proximal portion 112. In so doing, the pressure increase causes valve member 120 to open, releasing microbial reducing agent "MRA" into distal cavity 114a.

It is contemplated that an indicator window (not shown) may be provided in distal portion 114 to provide the user with a visual indication that the microbial reducing agent "MRA" has been pressed or squeezed into distal cavity 114a. Alternatively, housing 110 may be partially or completely formed of a transparent or translucent material enabling a user to visually notice the release of the microbial reducing agent "MRA" into distal cavity 114a.

As the microbial reducing agent "MRA" is released into distal cavity 114a of distal portion 114, the microbial reducing agent "MRA" is directly absorbed into absorbing member 122 or passed through backing member 124 and then into absorbing member 122 as well as transported through at least one aperture 124a to directly contact outer surface 18 of septum 12. As the microbial reducing agent "MRA" is absorbed into the absorbing member 122 the microbial reducing agent "MRA" further comes into contact with outer surface 18 of septum 12 exerting a chemical/biological cleansing action thereon and thus reducing any microbial contamination that may exist on outer surface 18 of septum 12.

Any air present in distal cavity 114a, during the pressing of membrane 118, may be vented through the coupling members 14a and 114c. In this manner, filling of distal cavity 114a with the microbial reducing agent "MRA" is facilitated. Alternatively, venting may be provided through a vent or port (not shown) formed in distal portion 114.

In order to further reduce the potential existence of microbial contaminants on the outer surface 18 of septum 12, an appropriate period of time, commensurate in scope with the type of microbial reducing agent "MRA" being used, is permitted to lapse prior to the removal of medical device 100 from needleless connector 10. Additionally, the microbial reducing agent "MRA" may be released into distal cavity 114a of distal portion 114 immediately following the connection of medical device 100 to needleless connector 10 to achieve an instantaneous microbial reducing environment for outer surface 18 of septum 12. In this manner, medical device 100 provides further prevention of microbial contamination of septum 12 throughout the period of time in between medical interventions.

Figure 1D:
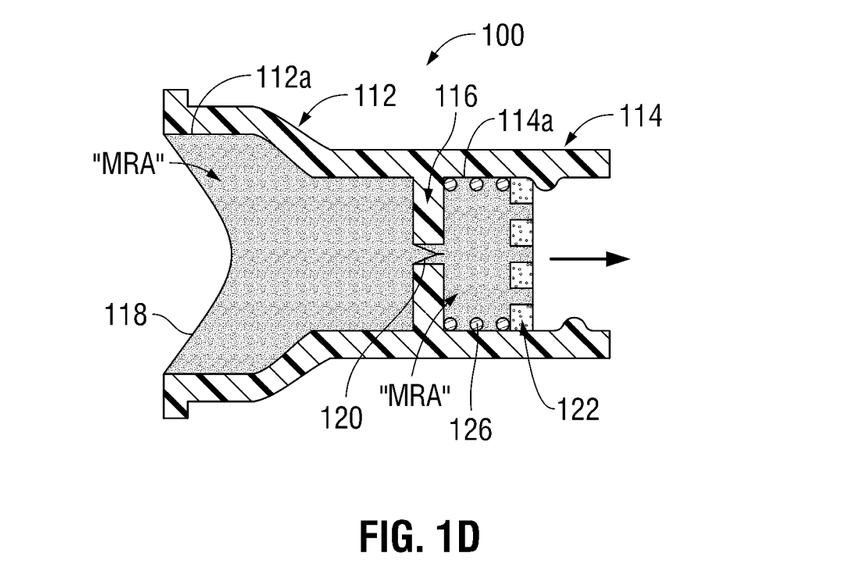
FIG. 1D is a schematic, longitudinal, cross-sectional view of the medical device of FIGS. 1A-1C, shown in a used condition, disconnected from the needleless connector.

In operation, as seen in FIG. 1D, as medical device 100 is removed or disconnected from needleless connector 10, for example, as by rotation, biasing member 126 maintains absorbent member 122 in contact with outer surface 18 of septum 12. In so doing, the rotation of medical device 100 relative to needleless connector 10 and, in particular, the outer surface 18 of septum 12, imparts a mechanical cleansing action by the absorbent member 122 against the outer surface 18 of septum 12.

Once medical device 100 has been completely removed or disconnected from needleless connector 10, medical device 100 may be appropriately discarded.

Figure 2A:
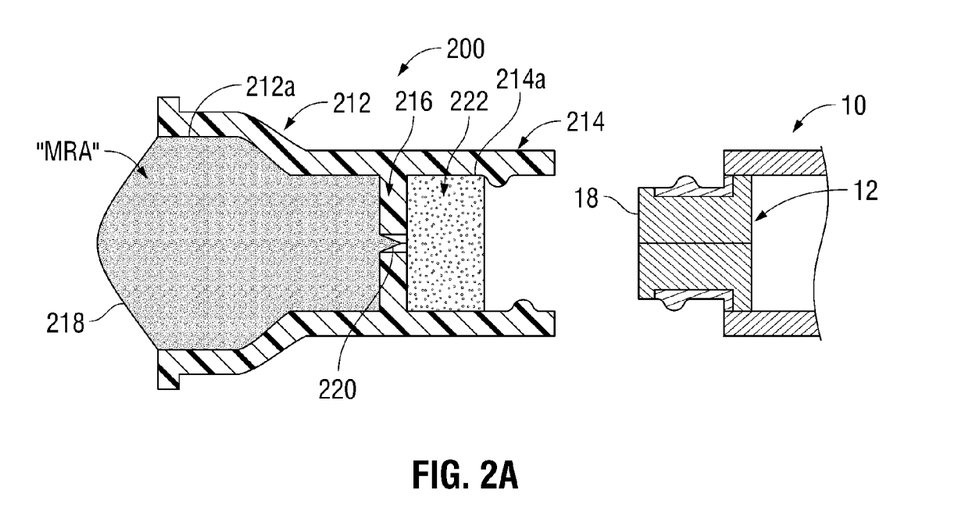
FIG. 2A is a schematic, longitudinal, cross-sectional view of a medical device according to another embodiment of the present disclosure, shown disconnected from the needleless connector and in an un-used condition.
Figure 2B:
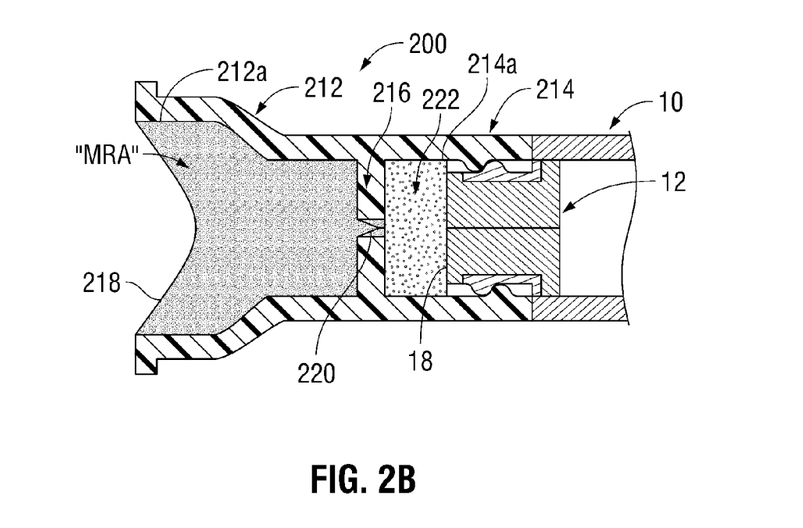
FIG. 2B is a schematic, longitudinal, cross-sectional view of the medical device of FIG. 2A, shown in a primed condition.

Turning now to FIGS. 2A-2B, a medical device, according to another embodiment of the present disclosure, is generally designated as 200. Medical device 200 is substantially similar to medical device 100 and thus will only be discussed in detail herein to the extent necessary to identify differences in construction and operation thereof.

As seen in FIGS. 2A-2B, medical device 200 does not include a biasing member interposed between partition 216 and absorbent member 222, in the manner of medical device 100. Instead, medical device 200 includes a resilient absorbent member 222 disposed within distal cavity 214a of distal portion 214. It is contemplated that absorbent member 222 may be relatively thicker than absorbent member 122 and may include at least one aperture formed therethrough (not shown).

In use, as medical device 200 is connected to needleless connector 10, absorbent member 222 is compressed, as seen in FIG. 2B. Prior to accessing needleless connector 10, membrane 218 is pressed, thus expelling the microbial reducing agent "MRA" from proximal cavity 212a, through valve member 220, into absorbent member 222 disposed within distal cavity 214a. As the microbial reducing agent "MRA" is absorbed into the absorbing member 222 the microbial reducing agent "MRA" comes into contact with outer surface 18 of septum 12 exerting a chemical/biological cleansing action thereon and thus reducing any microbial contamination that may exist on outer surface 18 of septum 12.

In operation, similar to medical device 100, as medical device 200 is removed or disconnected from needleless connector 10, for example, as by rotation, the resiliency of absorbent member 222 helps to maintain absorbent member 222 in contact with outer surface 18 of septum 12 as absorbent member 222 expands upon the disconnection of medical device 200 from needleless connector 10. In so doing, the rotation of medical device 200 relative to needleless connector 10 and, in particular, the outer surface 18 of septum 12, imparts a mechanical cleansing action by the absorbent member 222 against the outer surface 18 of septum 12.

Figure 3A:
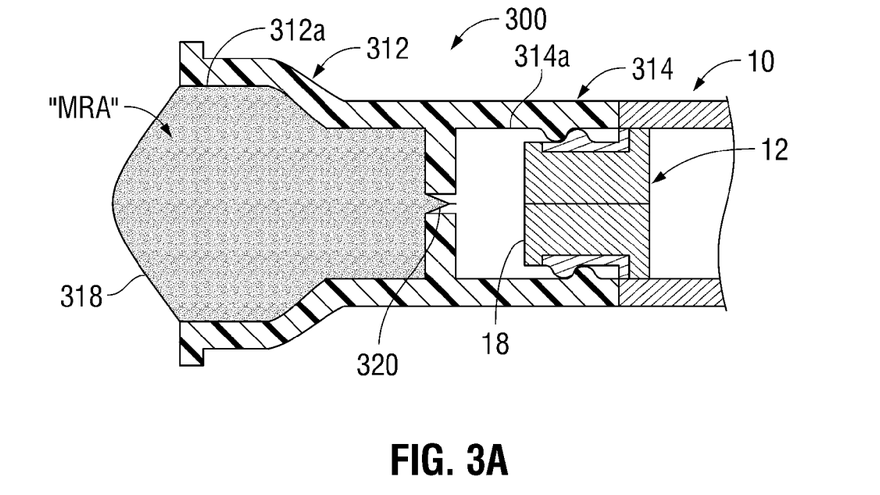
FIG. 3A is a schematic, longitudinal, cross-sectional view of a medical device according to yet another embodiment of the present disclosure, shown connected to the needleless connector and in an un-used condition.
Figure 3B:
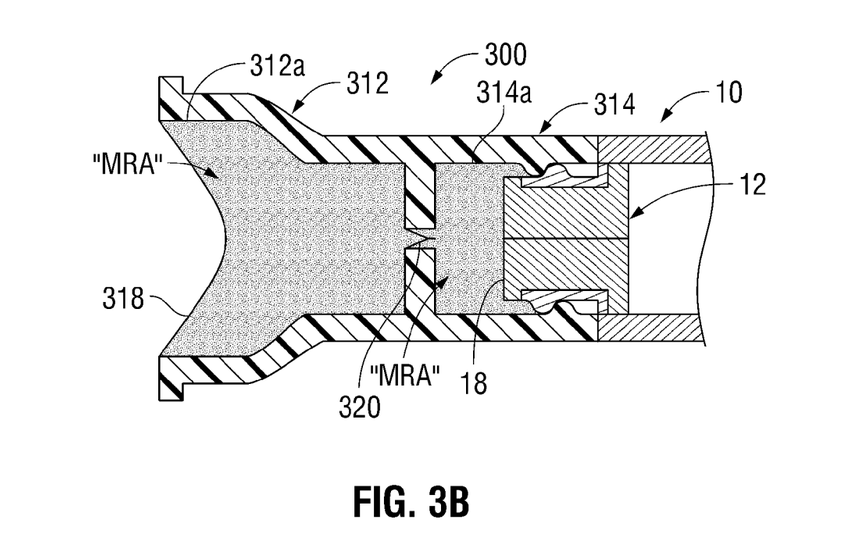
FIG. 3B is a schematic, longitudinal, cross-sectional view of the medical device of FIG. 3A, shown in a primed condition.

Turning now to FIGS. 3A-3B, a medical device, according to another embodiment of the present disclosure, is generally designated as 300. Medical device 300 is substantially similar to medical devices 100 or 200 and thus will only be discussed in detail herein to the extent necessary to identify differences in construction and operation thereof.

As seen in FIGS. 3A-3B, medical device 300 does not include a biasing member interposed or an absorbent member disposed within a distal cavity 314a of distal portion 314 thereof, in the manner of medical device 100. Instead, distal cavity 314a of medical device 300 is an open and/or empty cavity.

In use, prior to accessing needleless connector 10, membrane 318 is pressed, thus expelling the microbial reducing agent "MRA" from proximal cavity 312a, through valve member 320, into distal cavity 314a. As the microbial reducing agent "MRA" is expressed into distal cavity 314a the microbial reducing agent "MRA" comes into contact with outer surface 18 of septum 12 exerting a chemical/biological cleansing action thereon and thus reducing any microbial contamination that may exist on outer surface 18 of septum 12.

Figure 4A:
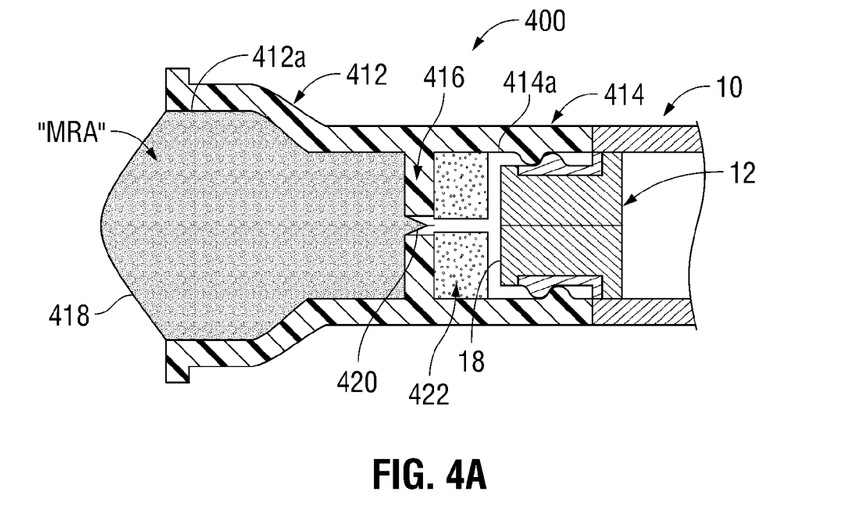
FIG. 4A is a schematic, longitudinal, cross-sectional view of a medical device according to still another embodiment of the present disclosure, shown connected to the needleless connector and in an un-used condition.
Figure 4B:
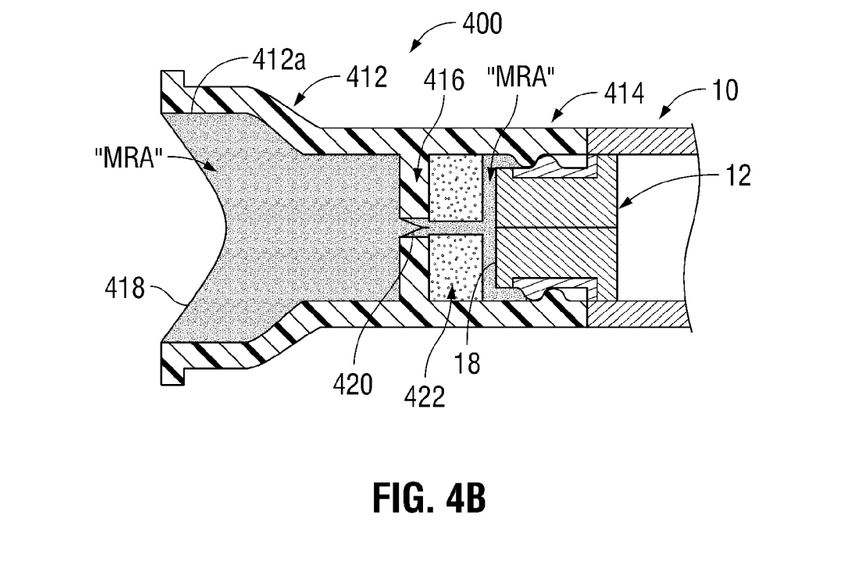
FIG. 4B is a schematic, longitudinal, cross-sectional view of the medical device of FIG. 4A, shown in a primed condition.

Turning now to FIGS. 4A-4B, a medical device, according to another embodiment of the present disclosure, is generally designated as 400. Medical device 400 is substantially similar to medical device 200 and thus will only be discussed in detail herein to the extent necessary to identify differences in construction and operation thereof.

As seen in FIGS. 4A-4B, medical device 400 includes an absorbent member 422 disposed within distal cavity 414a and in contact with partition 416. It is contemplated that absorbent member 422 may be dimensioned such that absorbent member 422 does not contact outer surface 18 of septum 12 when medical device 400 is connected to needleless connector 10. Absorbent member 422 functions to direct the initial amount of microbial reducing agent "MRA" to outer surface 18 of septum 12 as well as to minimize the amount of microbial reducing agent "MRA" that may exit distal cavity 414a upon the disconnection of medical device 400 from needleless connector 10.

In use, prior to accessing needleless connector 10, membrane 418 is pressed, thus expelling the microbial reducing agent "MRA" from proximal cavity 412a, through valve member 420, into distal cavity 414a. As the microbial reducing agent "MRA" is expressed into distal cavity 414a some microbial reducing agent "MRA" is absorbed into absorbent member 422 and some microbial reducing agent "MRA" comes into contact with outer surface 18 of septum 12 exerting a chemical/biological cleansing action thereon and thus reducing any microbial contamination that may exist on outer surface 18 of septum 12.

As medical device 400 is removed or disconnected from needleless connector 10, some microbial reducing agent "MRA" remains absorbed in absorbent member 422 and thus relatively less microbial reducing agent "MRA" is spilled.

While chemical/biological and/or mechanical cleansing actions have been described during the disconnection of the medical devices from the needleless connectors, it is contemplated and within the scope of the present disclosure that the absorbent members may be pre-soaked with microbial reducing agent "MRA" prior to connection of the medical device to the needleless connectors. In this manner, a chemical/biological and/or mechanical cleansing action of the outer surface of the septum of the needleless connector may take place upon either the connection of the medical device to the needleless connector or the disconnection of the medical device from the needleless connector due to the frictional engagement of the absorbent member against the outer surface of the needleless connector.

It will be understood that the embodiments of the present disclosure which have been described are illustrative of some of the applications of the principles of the present invention. Various modifications may be made by those skilled in the art without departing from the true spirit and scope of the invention.

What is claimed is:

1. A medical device for use with a connector of an indwelling line, the medical device comprising:
   a housing including a proximal portion and a distal portion separated from one another by a transversely extending partition that functions as a dividing wall, the partition having at least one opening defined therein, wherein each of the proximal portion and the distal portion defines a respective proximal cavity and a distal cavity, and wherein the proximal and distal cavities are in fluid communication with one another through the at least one opening in the partition, and wherein the distal cavity comprises a first coupling member configured to receive a portion of a second coupling member of the connector of the indwelling line within the distal cavity of the housing in a mating relationship;
   a microbial reducing agent disposed within the proximal cavity of the proximal portion; and
   a deformable member enclosing an end of the proximal portion for maintaining the microbial reducing agent within the proximal cavity of the proximal portion, the deformable member being collapsible into the proximal cavity to force the microbial reducing agent from the proximal cavity into the distal cavity.

2. The medical device according to claim 1, further comprising a valve member supported by the partition for enabling selective fluid communication between the proximal cavity and the distal cavity.

3. The medical device according to claim 2, further comprising an absorbent member disposed within the distal cavity.

4. The medical device according to claim 3, wherein the absorbent member is dimensioned to contact the connector of the indwelling line when the medical device is connected thereto.

5. The medical device according to claim 3, wherein the absorbent member is in contact with the partition.

6. The medical device according to claim 3, wherein the absorbent member is axially slidably disposed within the distal cavity.

7. The medical device according to claim 6, further comprising a biasing member interposed between the partition and the absorbent member, wherein the biasing member maintains the absorbent member at a distal-most location.

8. The medical device according to claim 7, further comprising a backing member supporting the absorbent member.

9. The medical device according to claim 8, wherein the backing member is at least one of porous and permeable.

10. The medical device according to claim 3, wherein the absorbent member is resilient.

11. The medical device according to claim 3, wherein the absorbent member contacts an outer surface of the connector of the indwelling line when the medical device is connected to the connector of the indwelling line.

12. The medical device according to claim 11, wherein the absorbent member exerts a mechanical cleansing action on at least a portion of the outer surface of the connector of the indwelling line upon a disconnection of the medical device from the connector of the indwelling line.

13. The medical device according to claim 3, wherein the microbial reducing agent is transferable to the absorbent member at least one of:
   prior to an attachment of the medical device to the connector of the indwelling line; and
   after an attachment of the medical device to the connector of the indwelling line;
   whereby the absorbent member exerts a chemical/biological and a mechanical cleansing action on an outer surface of the connector of the indwelling line upon at least one of connection and disconnection of the medical device to and from the connector of the indwelling line.

14. The medical device according to claim 2, wherein the valve member is a duck-bill valve.

15. The medical device according to claim 1, wherein the microbial reducing agent is transferable from the proximal cavity to the distal cavity upon exertion of a sufficient force on the deformable member.

16. The medical device according to claim 15, wherein the microbial reducing agent is transferred through the opening in the partition.

17. The medical device according to claim 16, wherein the microbial reducing agent is transferred through a valve member.

\* \* \* \* \*